United States Patent [19]
Früngel

[11] 3,986,023
[45] Oct. 12, 1976

[54] DEVICE FOR MEASURING OPTICAL CHARACTERISTICS OF THE ATMOSPHERE OF AN AIRFIELD

[76] Inventor: Frank Früngel, Herwigredder 105 a, 2000 Hamburg 56, Germany

[22] Filed: June 12, 1975

[21] Appl. No.: 585,797

[30] Foreign Application Priority Data

June 14, 1974 Germany............................ 2428901

[52] U.S. Cl. ................................. 250/239; 240/1.2; 240/84; 250/574; 356/103; 356/201
[51] Int. Cl.² ........................................ G01D 21/00
[58] Field of Search...................... 240/1.2, 25, 84; 250/239, 574, 564; 356/51, 103, 201, 207, 208

[56] References Cited
UNITED STATES PATENTS

| | | | |
|---|---|---|---|
| 2,207,097 | 7/1940 | Logan, Jr. ...................... | 250/238 X |
| 2,827,561 | 3/1958 | Kennedy, Jr. ..................... | 240/1.2 X |
| 3,162,373 | 12/1964 | Biggs et al. .......................... | 240/1.2 |
| 3,323,409 | 6/1967 | Früengel .............................. | 356/51 |

*Primary Examiner*—Alfred E. Smith
*Assistant Examiner*—T. N. Grigsby
*Attorney, Agent, or Firm*—Michael J. Striker

[57] ABSTRACT

An upright tubular housing has a lower end portion connectable to the ground, and an upper end portion. Arrangements for emitting and/or receiving light pulses are mounted in the lower end portion of the housing and a deflecting mirror is mounted in the upper end portion for deflecting the light pulses between a vertical and a substantially horizontal path. A break-away zone is formed in the lower end portion in the region where the same is connectable to the ground so that in the event of collision with an aircraft the housing will break away at this zone to thereby reduce the collision danger to the aircraft.

17 Claims, 2 Drawing Figures

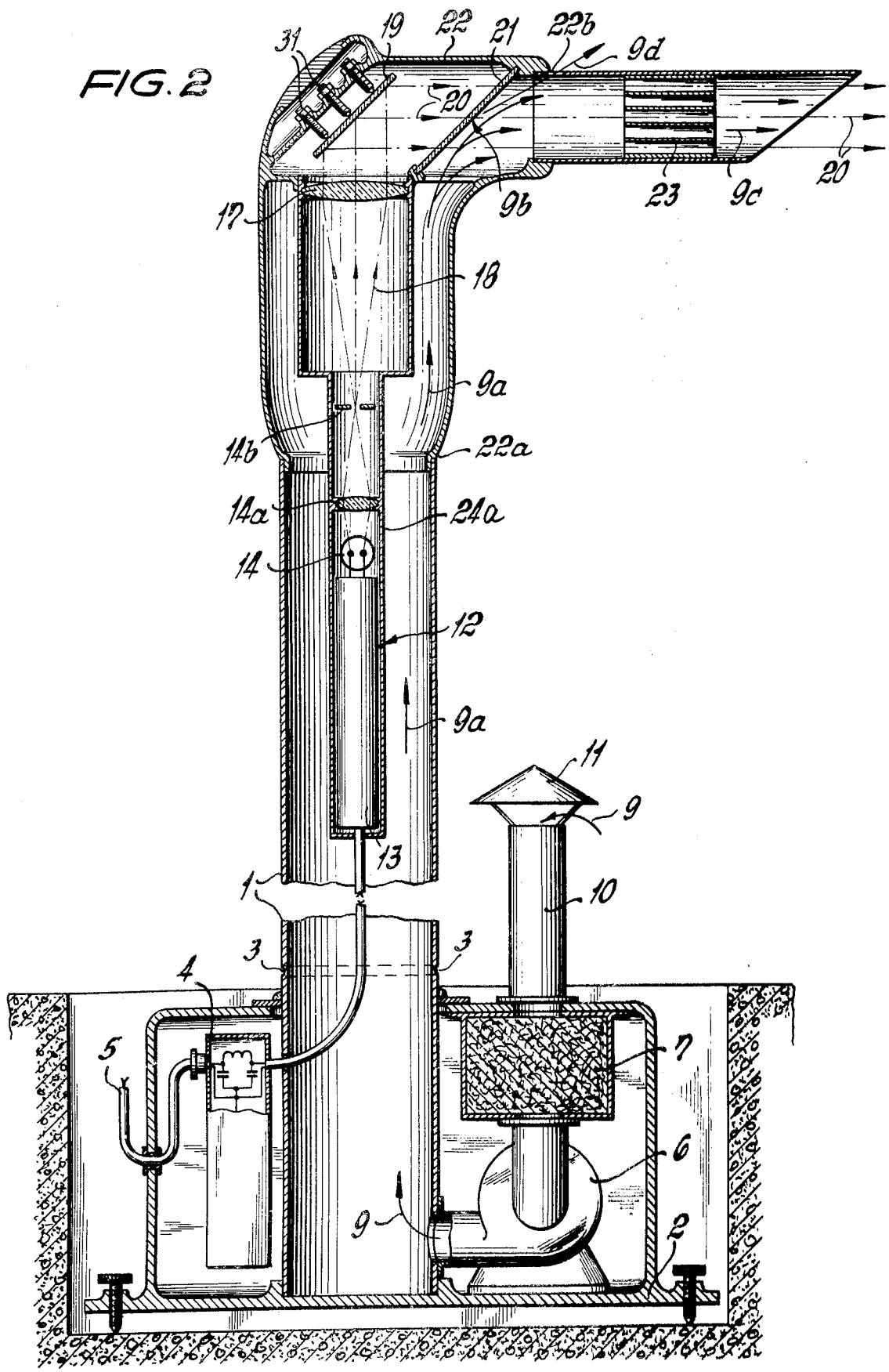

DEVICE FOR MEASURING OPTICAL CHARACTERISTICS OF THE ATMOSPHERE OF AN AIRFIELD

BACKGROUND OF THE INVENTION

The present invention relates to a device for measuring optical characteristics of the atmosphere, and more particularly to a device which is especially intended for measuring optical charcteristics of the atmosphere of an airfield.

Devices for measuring optical characteristics of the atmosphere, for example fog, smog for the like, are already known. They are usually constructed as transmissometers or optical back scatter measuring devices. For further details reference may be had to U.S. Pat. Nos. 3,672,775; 3,808,430 and 3,323,409, in which devices of this general type are disclosed in detail.

Such devices are used, inter alia, to measure the visibility in the atmosphere over airfields. They emit and/or receive light pulses and operate on the principle of comparing the intensity of the received light pulses with the intensity of the emitted light pulses, the detected variation then being a measure of the visibility in that atmospheric region through which the light pulses have travelled. Current international air safety regulations require that the measurements must be taken (i.e. that the light beams must travel) at a certain height above the surface of an airfield, which height is currently 2.80 meters above the surface, because the cockpits of the presently most frequently flown aircraft are located at this height above the ground when the aircraft touches ground.

The devices of the prior art employ upright vertical tubes at or near the top of which the electrical and optical components are mounted which are required for emitting and/or receiving the light pulses. Thus, the major portion of the mass of this prior-art device is located at or near the current measuring level of 2.80 meters, which brings with it the disadvantage that in the event of the collision of an aircraft with one of these devices significant damage to the aircraft can be expected to occur since the aircraft will collide with that part of the device at which the largest portion of the mass of the device is located. This danger exists particularly in the case of smaller aircraft, such as recreational aircraft, small business jets and the like, which because of their relatively low weight can be more readily deflected off the runway by sudden lateral winds than the larger commercial craft.

A proposal has been made in the prior art to so mount these devices that if a colliding aircraft engages a feeler of the device, the device will flip away for which purpose it is hingedly mounted. However, given the landing speeds of the modern aircraft it will be understood that the reaction time of a device constructed in this manner is too long to avoid a collision and the resulting danger.

Moreover, th prior-art devices of the type in question have the further disadvantage that the protective cover, through which the outgoing or incoming light pulses travel, tend to become obscured because they are not protected against such a possibility. Once so obscured, the intensity of the outgoing and/or incoming light beams will be falsified and this will influence the measured results. The problem exists not only in the event of rain or snow, but also — and particularly — as the result of deposition of pollutants — e.g. combustion products — resulting from the engines of the aircraft themselves. The combustion gases emitted by the engines of modern aircraft during starting and landing carry with them extremely small aerosols which travel at high diffusion speed and tend to form a fine milky coating on optical surfaces; all proposals made heretofore in the prior art for preventing the formation of such coatings have failed.

SUMMARY OF THE INVENTION

It is a general object of the present invention to avoid the disadvantages of the prior art.

More particularly, it is an object of the present invention to provide an improved device for measuring optical characteristics of the atmosphere of an airfield in which the danger of damage to an aircraft colliding with the device is substantially reduced.

A further object of the invention is to provide such a device in which the degree of measuring accuracy is significantly increased over those known from the prior art.

In keeping with these objects, and with others which will become apparent hereafter, one feature of the invention resides in a device for measuring optical characteristics of the atmosphere of an airfield which, briefly stated, comprises an upright tubular housing having a lower end portion connectable to the ground, and an upper end portion. Means is provided in the lower end portion of the housing for emitting and/or receiving light pulses. A deflecting mirror is mounted in the upper end portion for deflecting the light pulses between a vertical and a substantially horizontal path. A break-away zone is formed in the lower end portion in the region where the same is connectable to the ground, so that in the event of collision with an aircraft the housing will break away at this zone to thereby reduce the collision damage to the aircraft. The greatest part of the mass of the device, which is constituted by the means for emitting and/or receiving light pulses, is now located in the lower end portion of the tubular housing so that damage to an aircraft colliding with the upper end portion of the housing, which is preferably of a light-weight metal such as aluminum in order to further reduce the mass, cannot cause any severe damage to the aircraft. A further advantage of using a tubular housing of light-weight metal having high thermal conductivity is the fact that due to its tubular configuration it has a high mechanical bending resistance and thus does not readily bend or flex, but at the same time has excellent thermal conductivity so that heating of one side by the rays of the sun does not lead — as was previously the case — to asymmetric heating of the housing with a resultant deformation of the housing. Rather, the entire housiing is uniformly heated. The housing may also be coated with a corrosion-resistant infrared-penetrable paint in such a manner that a substantial portion of the incoming solar heat is reflected.

Only the deflecting mirror with its protective transparent cover and a hood is now provided at the upper end portion of the housing, and these components have low mass so that the danger of damage to a colliding aircraft is substantially reduced.

By producing a definite break-away zone formed in the lower end portion of the housing, in the region where the same is connectable to the ground, it is assured that in the event of a collision the housing will break away at a precisely defined location, namely at the break-away zone, and that it will do so readily without offering significant resistance to the colliding aircraft.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is a view similar to FIG. 1, but illustrating a different embodiment of the invention.

DESCRIPTION OF THE PREFERRED EMBODIMENTS

Figure 1:
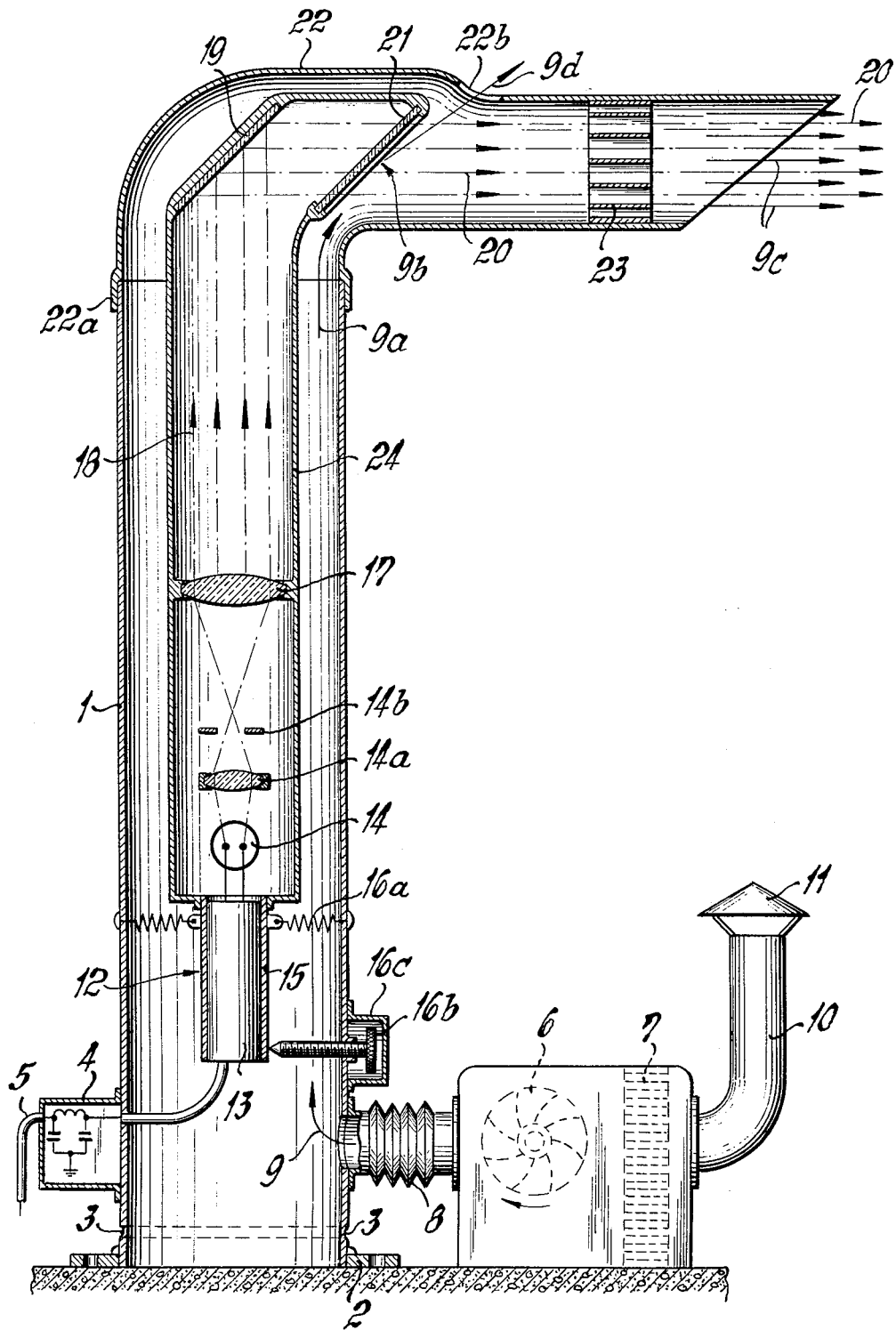
FIG. 1 is a somewhat diagrammatic vertical section through an embodiment of the invention.

In both embodiments of FIGS. 1 and 2 the illustrated device is of the type which constitutes an impulse-optical sender of an impulse-optical transmissometer. The operation of such senders, and of such transmissometers is known from the prior art, and reference may be had to the earlier-mentioned United States patents for further details.

In FIG. 1 a vertical tubular housing 1 of a lightweight metal such as aluminum or the like, is provided with a bottom flange 2 by means of which it is to be mounted on the ground, such as at the edge of or laterally adjacent to a runway. In the region of the flange the lower end portion of the tubular housing 1 is formed with a break-away zone 3 where the wall thickness of the housing 1 is reduced to assure that in the event of collision with an aircraft it will break at this zone 3. Advantageously, the wall thickness of the tubular housing 1 will be on the order of 2 millimeters and it is generally preferred if the housing 1 is of pure aluminum because pure aluminum has excellent thermal conductivity and light weight. The inner diameter of the tubular housing 1 may for example be 100 millimeters, annd the length of the housing, that is the vertical extent thereof, is on the order of 2.80 meters to comply with current international regulations. Adjacent the flange 2 a cable box is provided where cable connections are effected, and which may be provided with a lighting protector. Reference numeral 5 identifies a cable for the unit.

Also adjacent the flange, but separate from the housing 1, there is provided a blower 6 with a filter arrangement 7 which advantageously is composed of at least one coarse filter and at least one fine filter. The blower 6 and the filter arrangement 7 are mounted in a housing that is, as mentioned before, separate from the housing 1 and can be mounted on the ground. A flexible conduit 8 connects this housing with an inlet opening in the lower end portion of the housing 1 so that a stream of air propelled by the blower 6 can enter into the housing 1 in the direction of the arrow 9. Reference numeral 10 identifies the intake conduit through which the blower 6 draws air into the housing through the filter arrangement 7, and the open end of the intake conduit 10 is covered by a cap 11 which prevents rain and contaminants from dropping in.

An electro-optical unit 12 is mounted in the interior of the tubular housing 1, in the lower end portion of the same. The unit 12 may be a light-pulse sender and/or a light-pulse receiver. In the illustrted embodiment the unit 13 is assumed to consist of a stabilized power supply 15 with a capacitor-operated flash lamp 14. Devices of this type are known from the previously-mentioned prior art. It is preferred to surround the unit 12 at least in part with a tube 15 which serves to shield the component of the unit 12 against stray electrical fields that might interfere with its proper operation. The unit 12 may be mounted in the housing 1 by means of springs 16a, so that it can be adjusted in order to orient the optical axis, which should be vertical, relative to the housing 1. The adjustment can be effected by means of adjusting screws 16b of which there will be at least three provided, spaced equi-angularly about the circumference of the housing 1 (only one of the screws is shown). Reference numeral 16c identifies a cap which covers the head of the respective screw 16b.

The optical components of the device preferably comprise an intermediate lens 14a through which the light emitted by the spark discharge lamp or flash lamp 14 travels into an intermediate diaphragm 14b, from there to travel through a main lens 17 which is of the achromatic type and from whence it travels as a parallel light beam in the direction of the arrow 18 against an inclined deflecting mirror 19 provided in the upper end portion of the housing 1 which is constituted by a hood 22 that is connected to the vertical portion of the housing 1 by the flange 22a. The mirror 19 is inclined to the horizontal, through approximately 45°, so that the impinging light rays are deflected by and leave the hood 22 in the direction indicated by the arrows 20, i.e. in horizontal direction.

The stream of air coming from the blower 6 and having been filtered by the filter arrangement 7, travels through the annular space defined between the tube 15 and the inner wall of the housing 1 in upright direction. Upwardly of the tube 15 is preferably provided a further tube 24 which surrounds the optical components 14a, 14b and 17 and which extends to the deflecting mirror 19 and has opposite the mirror 19 an opening that is closed by a protective cover in form of a glass plate 21 which prevents access of the atmosphere to the mirror 19. The air stream thus travels in the annular path defined between the tubes 15, 24 on the one hand and the inner surface bounding the housing 1 on the other hand, until it reaches the constricted portion of the path where the air flow is indicated with reference numeral 9a. It is there accelerated prior to its impingement upon the outwardly directed surface of the protective glass plate 21 at 9b. Upon such impingement the air will either travel outwardly through the open end of the hood 22 in the direction of the arrow 9c, or if the hood is provided with an outlet opening 22b as illustrated, the air will travel in the direction of the arrow 9d out through this opening 22b in a path in which it includes an acute angle with horizontal. Because of the constricted flow path at 9a the flow speed of the air is highest at 9b, i.e. when it impinges the exposed surface of the glass plate 21 on which contaminants may tend to settle, so that it will reliably prevent the deposition of such contaminants. The cover or hood 22 is preferably made of a particularly light-weight material, for example aluminum or even a synthetic plastic, and can be removed for purposes of adjustment or repair.

In the case of transmissometers having a long measuring base a honeycomb filter 23 may be mounted in the hood 22 to assure a parallel guidance of the air flow so that the air flow will leave the hood 22 in a laminar flow. If the measuring base is short and it is important that the portion of the atmosphere directly outwardly adjacent the outlet of the hood 22 not be disturbed by the outflowing air 9c, then it is preferable to provide the opening 22b and to let the air escape in the direction of the arrow 9d.

The interior of the tube 24 may be filled with dry air and may of course be appropriately sealed, and due to the presence of the tube 24 accommodating the optical components the entire arrangement can be removed as a unit in toto. Despite this, it is assured that a strong air flow constantly flows at high speed over the surface 21 of the glass plate and prevents a coating from becoming deposited thereon which would disadvantageously influence the accuracy of the measurements made.

If the unit 12 is only of the type that emits light pulses, as in the embodiment of FIG. 1, then a similar arrangement to the one illustrated in FIG. 1 can be provided which in place of a light-emitting unit 12 will contain a light-receiving unit of the type disclosed in the prior art and which will then receive the light pulses emitted by the unit 12 shown in FIG. 1. Of course, both a light-emitting sand a light-receiving unit can be incorporated in one and the same device if an exterior reflector is used that reflects the emitted pulses back into the housing.

The mounting of the blower 6 with the associated components at the bottom of the tubular housing 1, and separate therefrom, assures that the mass of the housing 1 is not increased by the presence of this device. The housing accommodating the blower 6 may, incidentally, be provided with suitable heating means, such as an electric resistance heater or the like (not shown but known per se in the art) by means of which the air stream propelled by the blower 6 can be heated in order to melt off snow and ice that may tend to form on the surface of the glass plate 21. The constriction at 9a could be configurated differently then illustrated, or could be formed by different means; what is important is that the air stream should be accelerated as a result of its presence and should have a high flow speed at the time it impinges at 9b upon the surface of the glass plate 21.

The embodiment of FIG. 2 is largely similar to that of FIG. 1 and like reference numerals have been employed to identify like components.

FIG. 2 differs from FIG. 1 in that the bottom portion of the housing 1 is received in a pit formed in the ground, for example in a concreted runway or a separate mounting pad, so that the blower 6 and the cable box 4 are located below ground. This arrangement is even more advantageous in terms of the safety requirements of international air travel regulations.

In FIG. 2 the separate tube 15 has been omitted and the tube 24a is of lesser diameter than in FIG. 1 and accommodates the unit 12 within it. The mounting springs 16a and the adjusting screws 16b have been omitted. Instead, the embodiment of FIG. 2 comprises adjusting screws 31 by means of which the angular position of the deflecting mirror 19 can be adjusted. This increases the mass at the upper end of the device by only a few grams but makes possible a ready adjustment of the inclination of the mirror 19.

The sender or transmitter in FIG. 2 may utilize integrated circuits so that, counting the required shielding, the respective unit will weigh only approximately 2 pounds. The diameter of such units, i.e. the unit 12, need not be greater than about 5 centimeters and the vertical height or length is approximately 30 centimeters.

While the unit 12 is shown located in the lower end portion of the housing, but not at the bottom end thereof, it will be evident that there is no reason why the unit 12 could not be further lowered into the lower end shown in FIG. 2, i.e. to the vicinity of the inlet through which the air stream 9 enters, in order to further decrease the effective mass in the upper end portion of the device.

It will be understood that each of the elements described above, or two or more together, may also find a useful application in other types of constructions differing from the types described above.

While the invention has been illustrated and described as embodied in a device for measuring optical characteristics of the atmosphere of an airfield, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A device for measuring optical characteristics of the atmosphere of an airfield, comprising an upright tubular housing having a lower portion connectable to the ground, and an upper portion; an electro-optical light pulse unit means in said lower portion of said housing; a deflecting mirror in said upper portion for deflecting said light pulses between a vertical and a substantially horizontal path; flow-generating means adjacent said lower portion for directing a stream of air through said tubular housing; and means for shielding said electro-optical means from said air stream, comprising a shielding tube mounted within said tubular housing and surrounding said electro-optical means so as to prevent access of contaminants contained in said air stream.

2. A device as defined in claim 1; further comprising a protective transparent cover extending across said mirror and protecting the same from the ambient atmosphere.

3. A device as defined in claim 1; further comprising a protective transparent cover extending across said mirror and having one surface facing toward and another surface facing away from the same; and said flow-generating means adjacent said lower portion for directing said stream of air through said tubular housing and against said other surface of said transparent cover.

4. A device as defined in claim 1; further comprising a protective transparent cover extending across said mirror and having one surface facing toward and another surface facing away from the same; and said flow-generating means adjacent said lower portion for directing said stream of heated air through said tubular housing and against said other surface of said transparent cover.

5. A device as defined in claim 1; further comprising a protective transparent cover extending across said mirror and having one surface facing toward and another surface facing away from the same; and said flow-generating means adjacent said lower portion for directing said stream of air through said tubular housing and against said other surface of said transparent cover, said housing having an inner surface which at least in part bounds a constriction in the flow path for said stream of air upstream of said transparent cover.

6. A device as defined in claim 1; further comprising a protective transparent cover extending across said mirror and having one surface facing toward and another surface facing away from the same; and said flow generating means adjacent said lower portion for directing said stream of air through said tubular housing and against said other surface of said transparent cover, said housing having an outlet opening through which said stream of air exits in a direction which includes an acute angle with the horizontal.

7. A device as defined in claim 1, wherein said electro-optical means comprises electronic and optical components which are connected to form a unit that can be replaced in toto.

8. A device as defined in claim 1, wherein said electro-optical means comprises optical components; and further comprising set screws for adjusting the orientation of said optical components relative to said housing.

9. A device as defined in claim 1; and further comprising adjusting screws for adjusting the orientation of said mirror relative to said housing.

10. A device as defined in claim 1, wherein said flow-generating means is mountable in a pit in the ground.

11. A device as defined in claim 1, wherein said electro-optical means comprises a detector unit for receiving light pulses.

12. A device as defined in claim 1; and further comprising a break-away zone formed in said lower portion in the region where the same is connectable to the ground, so that in the event of collision with an aircraft said housing will break away at said zone to thereby reduce the collision damage to the aircraft.

13. A device as defined in claim 1, said electro-optical means comprising electronic components; and wherein said shielding tube is coaxially mounted in said housing and surrounds at least said electronic components so as to define with said housing an annular flow space for said air stream.

14. A device as defined in claim 1; further comprising a protective transparent cover extending across said mirror and having one surface facing toward and another surface facing away from the same; and wherein said flow-generating means is adjacent said lower portion for directing said stream of air through an opening in said lower portion into said tubular housing and against said other surface of said transparent cover; and flexible conduit means connecting said flow-generating means with said opening.

15. A device as defined in claim 1; wherein said flow-generating means comprises a blower adjacent the ground, separate from said housing and operative for directing said stream of air through said housing.

16. A device as defined in claim 1; further comprising a protective transparent cover extending across said mirror and having one surface facing toward and another surface facing away from the same; said flow-generating means adjacent said lower portion for directing said stream of air through said tubular housing and against said other surface of said transparent cover; and filter means for filtering said air.

17. A device as defined in claim 1, wherein said filter means comprises at least one coarse filter and at least one filter.

* * * * *